(12) United States Patent
Ramaekers (10) Patent No.: US 9,463,218 B2
(45) Date of Patent: Oct. 11, 2016

(54) TRANSFER FACTOR FOR IMPROVING FERTILITY

(71) Applicant: CortControl, Inc., Santa Cruz, CA (US)

(72) Inventor: Joseph Ramaekers, Aptos, CA (US)

(73) Assignee: CORTCONTROL, INC., Santa Cruz, CA (US)

( * ) Notice: Subject to any disclaimer, the term of this patent is extended or adjusted under 35 U.S.C. 154(b) by 0 days.

(21) Appl. No.: 14/121,670

(22) Filed: Oct. 6, 2014

(65) Prior Publication Data

US 2016/0095900 A1 Apr. 7, 2016

Related U.S. Application Data

(63) Continuation-in-part of application No. 13/999,875, filed on Mar. 29, 2014, now abandoned, which is a continuation-in-part of application No. 13/729,923, filed on Dec. 28, 2012, now Pat. No. 9,125,875, which is a continuation-in-part of application No. 12/325,199, filed on Nov. 30, 2008, now Pat. No. 8,357,663, said application No. 13/999,875 is a continuation-in-part of application No. 13/843,581, filed on Mar. 15, 2013, which is a continuation-in-part of application No. 13/718,319, filed on Dec. 18, 2012, which is a continuation-in-part of application No. 12/631,745, filed on Dec. 4, 2009, which is a continuation of application No. 11/492,464, filed on Jul. 24, 2006.

(60) Provisional application No. 61/964,100, filed on Dec. 24, 2013, provisional application No. 61/964,100, filed on Dec. 24, 2013.

(51) Int. Cl.
| | |
|---|---|
| A61K 38/17 | (2006.01) |
| A61K 31/716 | (2006.01) |
| A61K 35/744 | (2015.01) |
| A23L 1/30 | (2006.01) |
| A23L 1/29 | (2006.01) |
| A23L 1/305 | (2006.01) |

(52) U.S. Cl.
CPC ............ *A61K 38/1709* (2013.01); *A23L 1/296* (2013.01); *A23L 1/305* (2013.01); *A23L 1/3014* (2013.01); *A61K 31/716* (2013.01); *A61K 35/744* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 2004/0156920 A1* | 8/2004 | Kane | 424/725 |
| 2007/0128253 A1* | 6/2007 | Ramaekers | 424/442 |
| 2009/0170774 A1* | 7/2009 | Ramaekers | 514/12 |

OTHER PUBLICATIONS

Cwikel et al., European Journal of Obstetrics & Gynecology and Reproductive Biology, 2004; 117: 126-131.*
Johnson & Everitt, "Infertility and Subfertility", in Essential Reproduction, Blackwell Science, Fifth edition, 2000; Chapter 15, p. 265.*
Weinstock, Progress in Neurobiology, 2001; 65: 427-451.*
FDA presentation entitled "Regulation of Medical Foods", presented on Mar. 1, 2012 and downloaded from www.fda.gov; 23 pages total.*
Csemicky, G. et al., "The Influence of Stress and State Anxiety on the outcome of IVF-treatment: Psychological and Endocrinological Assessment of Swedish Women Entering IVF-treatment," Acta Obstet Gynecol Scand 2000: 79:113-118.

* cited by examiner

*Primary Examiner* — Christina Borgeest
(74) *Attorney, Agent, or Firm* — Schwabe Williamson & Wyatt (57) ABSTRACT

A method of using a fertility enhancement food to improve human fertility. This fertility enhancement food consists of transfer factor, lactic acid generating bacteria, and/or glucans in appropriate combinations. The fertility food, administered correctly, reduces cortisol levels. High cortisol interferes with conception and stable pregnancies. Dosage amounts are adjusted for client weight. Consumption frequency may be adjusted in response to cortisol measurements. Typically, consumption of the fertility food begins seven or more days before planned conception.

19 Claims, 4 Drawing Sheets

TRANSFER FACTOR FOR IMPROVING FERTILITY

CROSS-REFERENCE TO RELATED APPLICATIONS

This application is a continuation-in-part of U.S. application Ser. No. 13/999,875 filed Mar. 29, 2014, which is currently pending. U.S. application Ser. No. 13/999,875 is a continuation-in-part of U.S. application Ser. No. 13/729,923 filed Dec. 28, 2012, which is a continuation- in-part of U.S. application Ser. No. 12/325,199 filed Nov. 30, 2008. U.S. application Ser. No. 13/999,875 filed Mar. 29, 2014 also claims priority to U.S. application Ser. No. 13/843,581 filed Mar. 15, 2013 and currently pending, which is a continuation-in-part of U.S. application Ser. No. 13/718,319 filed Dec. 18, 2012, which is a continuation in part of U.S. application Ser. No. 12/631,745 filed Dec. 4, 2009, which is a continuation of U.S. application Ser. No. 11/492,464 filed Jul. 24, 2006. U.S. application Ser. No. 13/999,875 also claims priority to U.S. Provisional Application 61/964,100 filed Dec. 24, 2013. Application Ser. Nos. 13/999,875, 13/729,923, 12/325,199, 13/843,581, 13/718,319, 12/631,745, 11/492,464, and 61/964,100 are incorporated in their entirely by reference into this instant application.

FIELD OF THE INVENTION

The invention relates to a method of administering fertility enhancement food comprising at least transfer factor and lactic acid generating bacteria to increase fertility in humans with high cortisol levels. In particular, fertility is increased by reducing cortisol in both men and women with the administered fertility enhancement food.

Claimed priority applications utilize the fertility enhancement food for non-human mammals. This application extends use to humans by modifying treatment periods, modifying administration frequency, and adjusting formulations based on monitoring feedback.

BACKGROUND OF THE INVENTION

High human cortisol is defined as cortisol levels that exceed the human population average.

In the United States, the number of women ages 15-44 with impaired fecundity (impaired ability to get pregnant or carry a baby to term) is 6.7 million. Multiple fertility clinics exist to help women with fertility issues.

Research indicates that stress is an important factor. Speculation about the correlation between stress and infertility is part of the prior art.

One fertility clinic broadcasts the following message: "The best fertility treatment is beating stress". A 2009 study at Emory University concluded that "We think there are women who have sub-clinical forms of stress and who are infertile as a result . . . . " More work on cortisol correlation was suggested in this Emory study. The study is informative, but does not recite a treatment method with transfer factor and lactic acid generating bacteria.

Although cortisol reduction has long been proposed as a way to enhance human fertility, no human-specific treatment method utilizing at least transfer factor and lactic acid generating bacteria has been fully enabled. Methods of treating infertility, which do not incorporate transfer factor and lactic acid generating bacteria into a fertility enhancement food, are outside the scope of the instant invention.

Cwikel et al. (European Journal of Obstetrics & Gynecology and Reproductive Biology, 117 (2004), pp. 126-131) teaches that stress levels contribute to infertility, and that cortisol levels are predictive of infertility. This study is informative. But it is outside the scope of the instant application because it does not provide a remedy based on fertility enhancement food comprising at least transfer factor and lactic acid generating bacteria.

Johnson and Everitt ("Infertility and Subfertility" in *Essential Reproduction*, Blackwell Science, Fifth edition, 2000; chapter 15, p. 265) connect stress and infertility issues. Cortisol is not specifically cited as a marker. And, there is no citation of a treatment method using at least transfer factor and lactic acid generating bacteria.

Stress is a broad term and carries connotations. Different observers may define stress in different symptomatic ways. Fortunately, stress is associated with a chemical marker. Cortisol is the major stress hormone, and cortisol measurement allows stress to be quantified.

The veterinary field was first to increase fertility in animals with a food-based approach. Ramaekers recites the food composition of transfer factor and lactic acid generating bacteria in U.S. Pat. No. 6,962,718. Use of the food composition to enhance livestock fertility is recited in U.S. application Ser. Nos. 13/729,923 and 13/843,581, which are currently pending. Low calving rates in cattle herds represent a large loss to a rancher. Birth rates increased when cortisol levels were intentionally lowered with a fertility enhancement food including transfer factor and lactic acid generating bacteria.

Cattle studies have repeatedly demonstrated that feeding a mixture of transfer factor and lactic acid generating bacteria increases fertility.

The experience of livestock is significant because the hormonal mechanism of stress is the same in all mammals. Humans generate the stress hormone, cortisol, in the same way as a goat, pig, cow, horse, or monkey. Basically, the pituitary releases ACTH (adrenocorticotropic hormone). Then ACTH stimulates the adrenal cortex to secrete cortisol.

Fertility improvement for humans is suggested in Ramaekers' U.S. publication 20090170774. However, optimal human treatment times and feeding frequencies were later determined to differ between humans and other mammals. These were first presented in application Ser. No. 13/999,875 by Ramaekers and Menear dated Mar. 29, 2014. This instant application focuses on method steps to optimize human fertility.

Cortisol has a positive value in the short term. It energizes the body for a fight or flight situation. But a cortisol excess over a long time is destructive. Fertility is one of the casualties.

Fertility clinics address infertility with a variety of treatments. Treatments commonly include drugs. Drug treatments may have side effects. In contrast, the mixture of transfer factor and lactic acid generating bacteria is a food, not a drug. Foods take longer to confer benefits than drugs. But, foods comprising transfer factor and lactic acid generating bacteria are inherently safe.

The consuming public now understands that foods possess more than basic nutrition (protein, carbohydrate, fat, etc.). For example, 95% of consumers agree that "certain foods have health benefits that go beyond basic nutrition and may reduce the risk of disease or other health concerns". More than 50% of consumers believe that foods can replace the use of drugs.

The Federal Drug Administration acknowledges this trend with the relatively new category of "Medical Foods". Medical Foods should be administered or monitored by a doctor, nutritionist, nurse, medical technician or equivalent health care professional. Medical foods are defined by the Federal Drug Administration in 21 CFR 101.9(j)(8).

A food-based fertility treatment option is needed that addresses root causes and avoids side effects. A food based treatment may be used in conjunction with other treatments.

BRIEF SUMMARY OF THE INVENTION

This instant invention is a method of treating human infertility with a food that reduces human cortisol levels. The fertility enhancement food contains at least transfer factor and lactic acid generating bacteria. An infertility food treatment that includes consumption of transfer factor and lactic acid generating bacteria is within the scope of this invention. An infertility treatment that does not include consumption of transfer factor and lactic acid generating bacteria is outside the scope of this invention. Fertility enhancement food may include other components in conjunction with transfer factor and lactic acid generating bacteria.

One possible fertility enhancement mechanism involves progesterone. Reduced cortisol levels correlate with higher progesterone levels and enhanced fertility. Progesterone means "for gestation". Progesterone is necessary for healthy egg production, and the egg's stable attachment to the uterus. Progesterone is further necessary to feed and nourish the uterus during pregnancy, and, hence, support the fetus. Low progesterone is associated with early miscarriage and failure to reach full term. A second mechanism of cortisol-induced infertility is referred to as "polycystic ovary syndrome", which interferes with egg production. Again, high cortisol and low progesterone are involved.

However, this application is not limited by any specific mechanism. Claims are based on a food formulation that lowers cortisol and enhances fertility, regardless of the mechanism. Claims are based on data rather than theory.

Following is a condensed summary of the invention. By necessity, details are omitted in order to simply state the essence of the invention. Omitted details within this section should not be construed in a way that limits or alters the scope of the invention.

One preferred food composition used to treat infertility is a mixture of transfer factor and lactic acid generating bacteria. This composition is described in U.S. Pat. No. 6,962,718 issued to Joseph Ramaekers.

Another preferred food composition used to treat infertility is a mixture of transfer factor, lactic acid generating bacteria, and glucans. Glucans may be present as mushrooms. This composition is encompassed by Ramaekers' domineering U.S. Pat. No. 6,962,718, and contains one additional limitation (glucans).

Glucans have a long history of use to raise human and animal resistance. For example, Kane [U.S. publication number 2004/0156920 A1] teaches the use of 2 mg/kg/day for humans. But Kane does not suggest a combination of transfer factor, lactic acid generating bacteria, and/or glucans, which is required in this instant application.

Food compositions may be augmented with additives other than transfer factor, lactic acid generating bacteria, and glucans. The use of additives remains within the invention scope, providing that transfer factor and lactic acid generating bacteria are present.

Dosages of medical foods may be adjusted for patient weight. This is described by Ramaekers in Application Publication 20090170774, which is a priority document. At the bottom of Table 1 in Application Publication 20090170774, amounts are calculated for livestock weighing over 450 pounds and cats/dogs weighing as little as 8 pounds.

Humans will respond to dosage levels that mimic animal use. But, there are better options. Recommended human treatment durations and human frequency of consumption differ from other mammals. And optimal human treatments allow adjustment based on continual cortisol measurement when a health care professional recommends a change.

For example, livestock treatment periods responded to a 12 day treatment period with daily consumption. (Refer to FIGS. 3 and 4 in this disclosure, where the X-axis covers 12 days). That 12-day livestock program was largely based on the economics of ranching, rather than optimizing the outcome. To a rancher, fertility enhancement has to show a return on investment. A long treatment program might be prohibitive from a cost viewpoint.

In contrast, human fertility clients are interested in the optimal results. Treatment cost is important, but not primary. One preferred human treatment period is based on consumption prior to planned conception, and continued until a stable pregnancy is achieved. Another preferred human treatment period is based on consumption prior to planned conception, and continued through delivery.

Consumption 30 days prior to planned human conception is appropriate. However, consumption 7 days prior to planned conception may be sufficient for some couples. Because the fertility enhancement food is inherently safe, consumption more than 30 days prior to planned conception may be elected for extra assurance.

Human administration frequency has a wider range than other mammals. Humans consumption varies between five times per day and once per week. For livestock, consumption is typically fixed at once per day or once every second day.

The relative proportion of transfer factor, lactic acid generating bacteria, and glucans within a human dose may vary. Although typical proportions can be borrowed from animal testing (per Ramaekers in U.S. application Ser. Nos. 13/729,923 and 13/843,581), proportions may be modified to best serve each individual. Humans can imagine stressful situations, which stimulates cortisol production—just like a real stressful situation. Hence, the variation of response time is wider. Analytical feedback from cortisol measurements trigger proportion modification.

For some clients, transfer factor, lactic acid generating bacteria, and glucans are taken together. For other clients, transfer factor, lactic acid generating bacteria, and glucans are taken at different times during the day or week. Component separation and consumption at different times are within the scope of this invention. Separate consumption and was recited in Ramaekers' U.S. Publication 20070128253, which benefits this application. The human body performs the mixing.

Typical method-of-use steps include some or all of the following: (1) correlating high cortisol levels with infertility, (2) selecting the medical food dosage level, (3) beginning consumption of the medical food before planned conception, (4) continuing the fertility enhancement food up to nine months into the pregnancy, and (5) measuring cortisol levels between conception and birth.

Patent application Ser. No. 13/729,923 solved the infertility issue for livestock with (1) a combination of transfer factor and lactic acid generating bacteria, or (2) a combination of transfer factor, lactic acid generating bacteria, and glucans. Ramaekers (in Ser. No. 13/729,923) determined that feeding these combinations to livestock increased the calf birthrate, and lowered cortisol levels. For testing, bovine populations of 200-300 were divided into randomized test and control groups, and the control group was fed a placebo formulation.

Ramaekers' application publication number 20090170774 focuses on animal fertility enhancement, but also recites human application (see publication number 20090170774, paragraphs [0051] and [0057] on page 5).

Although method steps are altered, fertility data from livestock is probative for humans. This is based on four facts. First, cortisol biochemistry is the same among mammal species. Second, transfer factor works across species. Transfer factor from a cow lowers cortisol in horses, sheep, and humans. Third, lactic acid generating bacteria and glucans are utilized nutritionally the same way. Forth, human weight falls between the extreme weights of livestock and domestic pets. Extreme weights are cited in Table 1 of Ramaekers' publication number 20090170774.

Informal studies demonstrate the human response between lowered cortisol and either (1) a combination of transfer factor and lactic acid generating bacteria, or (2) a combination of transfer factor, lactic acid generating bacteria, and glucans. Feeding these foods to stressed athletes lowers the symptoms of cortisol excess, and win/loss records reflect it. College students consume these foods before final examinations to lower cortisol and get a better night's sleep and higher grades. Golfers score lower with cortisol-reducing food.

Response commonality between humans and other mammals is evident from a preponderance of data. Lowered cortisol measurements correlate to consuming transfer factor, lactic acid generating bacteria, and/or glucans. In turn, fertility is enhanced by lowering cortisol. Other stress hormones may also be lowered by consuming transfer factor, lactic acid generating bacteria, and/or glucans. Again, fertility enhancement food works for animals and humans, but the preferred method of treatment for humans differs from animals.

This application describes and claims the methodology differences.

Method claims presented in this application are based on subject matter that is jointly owned by the joint inventors. Method claims in the instant application include method steps that were not introduced earlier in U.S. application Ser. Nos. 13/729,923 and 13/843,581. As such, these claims are considered subject to the filing date of this current application. Fertility enhancement food formulations were cited in earlier priority documents, and are solely owned by Dr. Joseph Ramaekers. No instant claims are drawn to compositions.

Ramaekers (U.S. Publication 2009017774, published Jul. 2, 2009) discloses a fertility enhancement food including transfer factor. The utility was fertility improvement in males and female animals. In his disclosure, Dr. Ramaekers contemplates application to humans. However, the method claims were still directed toward livestock. In this instant application, claims are different because they are specific to humans, and the claims reflect recent understandings.

DETAILED DESCRIPTION OF THE INVENTION

Transfer factor is produced by leucocytes and lymphocytes. Transfer factor comprises small water soluble polypeptides of about 44 amino acids that stimulate or transfer cell mediated immunity from one individual to another.

The properties, characteristics and processes for obtaining transfer factor or transfer factors are discussed in U.S. Pat. Nos. 4,816,563; 5,080,895; 5,840,700, 5,883,224 and 6,468,534, the contents of which are hereby incorporated by reference into the present application.

Alternative sources of transfer factor include avian transfer factor, ova transfer factor, and colostrum from goats, pigs, horses and humans. This listing is not complete. In addition, combinations of transfer factors from multiple sources may be used in fertility formulations.

Although transfer factor can be extracted from colostrum, it is noteworthy that transfer factor and colostrum are not the same.

In certain embodiments of fertility enhancement, substantially purified transfer factor has a molecular weight of less than 10,000 Daltons.

Transfer factor is commercially available, and generally recognized as safe.

Lactic acid generating bacteria is an important component of the invented infertility medical food, and is GRAS (generally recognized as safe). Lactic acid generating bacteria support digestion and brain health. Lactic acid generating bacteria provide healthful effects that are found in non-pasteurized sauer kraut and cod liver oil. Within the intestinal tract, lactic acid generating bacteria are beneficial. It has been estimated that 80% of human health depends on beneficial intestinal bacteria.

A human body becomes stressed by poor digestion, and cortisol levels will reflect that stress. Lactic acid generating bacteria help reduce cortisol via improved digestion.

Glucans (polysaccharides) are known to support the immune system. When combined with transfer factor and lactic acid generating bacteria, a synergy is created. The combined effect on fertility is greater than the effect predicted from summing the individual components.

Although much emphasis is placed on female clients, male reproductive health and function is also improved by the feeding formulations comprising (1) transfer factor and lactic acid generating bacteria or (2) transfer factor, lactic acid generating bacteria, and glucans. This improved function may include quantity or quality of sperm produced by the male. Roughly one-third of infertility problems originate with the male.

Once high cortisol is diagnosed, the infertility treatment should address it. There may be several factors involved, but lowering cortisol is particularly important.

Most likely medicines will be prescribed, but medicines can have undesirable side effects.

In some cases, progesterone supplementation may be tried. But research has shown that this is not the ideal solution. Progesterone levels seldom return to stable-and-normal without first addressing cortisol levels.

One preferred fertility enhancement food is a mixture of transfer factor and lactic acid-generating bacteria. This composition is patented (Joe Ramaekers, U.S. Pat. No. 6,962,718, claim 6, issued Nov. 8, 2005). The method of specifically using transfer factor and lactic acid generating bacteria for treating human infertility is viewed as an improvement limitation on Ramaekers' existing commonly-owned composition patent. An improvement claim is presented in the claims section.

Another preferred fertility enhancement food is a mixture of transfer factor, lactic acid generating bacteria, and glucans. Glucans may be present as mushrooms. The method of using transfer factor, lactic acid generating bacteria, and glucans for treating infertility can also be viewed as two improvements to U.S. Pat. No. 6,962,718. The two improvements (limitations) are (1) the addition of glucans, and (2) the method of using the patented composition to enhance human fertility. An improvement claim is presented in the claims section.

Either fertility enhancement food may be augmented with additional additives. Example additives are minerals, probiotics, prebiotics, dimethyl glycine, ascorbic acid, Vitamin A, Vitamin D3, Vitamin E, Vitamin B1, Vitamin B2, Vitamin B12, dipotassium phosphate, potassium chloride, magnesium sulfate, calcium pantothenate, minerals, antioxidants, amino acids, nutraceuticals, inositol hexaphosphate (Ip6), mannans, olive leaf extract, and phytosterols. In certain preferred embodiments, mannans are derived from Aloe vera. In certain preferred embodiments, phytosterols may be derived from soya bean.

Probiotics additives include, but are not limited to *B. subtlis, B. longum, thermophilium, B. coagulans, E. faecium*, and *S. cerevisia, L. casei, L. plantarum, Pediococcus acidilacticii, Kluyveromyces marxianus* fragilis and combinations thereof.

The above listings do not include all possible additives. The food compositions may also include one or more of the following: carrier proteins such as serum albumin; buffers such as sodium acetate; fillers such as microcrystalline cellulose, lactose, corn and other starches; binding agents; sweeteners and other flavoring agents; coloring agents; and polyethylene glycol. Additives are well known in the art, and are used in a variety of formulations.

The relative proportion of transfer factor, lactic acid generating bacteria, and glucans within the fertility enhancement food may vary widely. Variation occurs among people, and variation occurs for a given person over time. Relative to livestock, human variation is wider because humans can imagine stressful situations. Cortisol levels react to imagined stress.

Reasonable component weight ranges are similar to ranges in Ramaekers application Ser. No. 13/729,923 for animal use. For transfer factor 0.05-50 mg/pound of body weight is appropriate. Reasonable weight ranges for lactic acid generating bacteria are 0.47-10 mg/pound of body weight. This is based on a nominal live count of $2.5 \times 10^6$ CFU/Ounce. Reasonable weight ranges for glucans are 0.1-10 mg/pound of body weight.

In most cases, dosages per pound of human body weight will be on the high side of the stated animal ranges to correct for human imagination. And dosages can change with time as cortisol levels fluctuate.

Periodic measurement of cortisol levels followed by dosage adjustment is appropriate before and during the pregnancy. Again, this is because humans can imagine stressful and peaceful situations. Cortisol levels increase in response to stressful thoughts, and subside with calming thoughts.

Another difference between human and animal methodology is the length of treatment. In one embodiment of the invention, human females are treated throughout the full nine months gestation. In contrast, infertile female animals are typically treated for periods of economically limited periods.

In one embodiment-human males begin treatment with fertility enhancement food 90 to 120 days before planned conception. This period is usually sufficient to address low sperm count and low sperm quality that are 2 (or more) standard deviations below the male population mean.

In another method embodiment, human males begin treatment with the infertility food composition 30 to 60 days before planned conception. This period is usually sufficient to address sperm count and sperm quality that are 1 standard deviation below the male population mean.

The above pre-conception treatment periods are guidelines rather than rigid rules.

Figure 3:
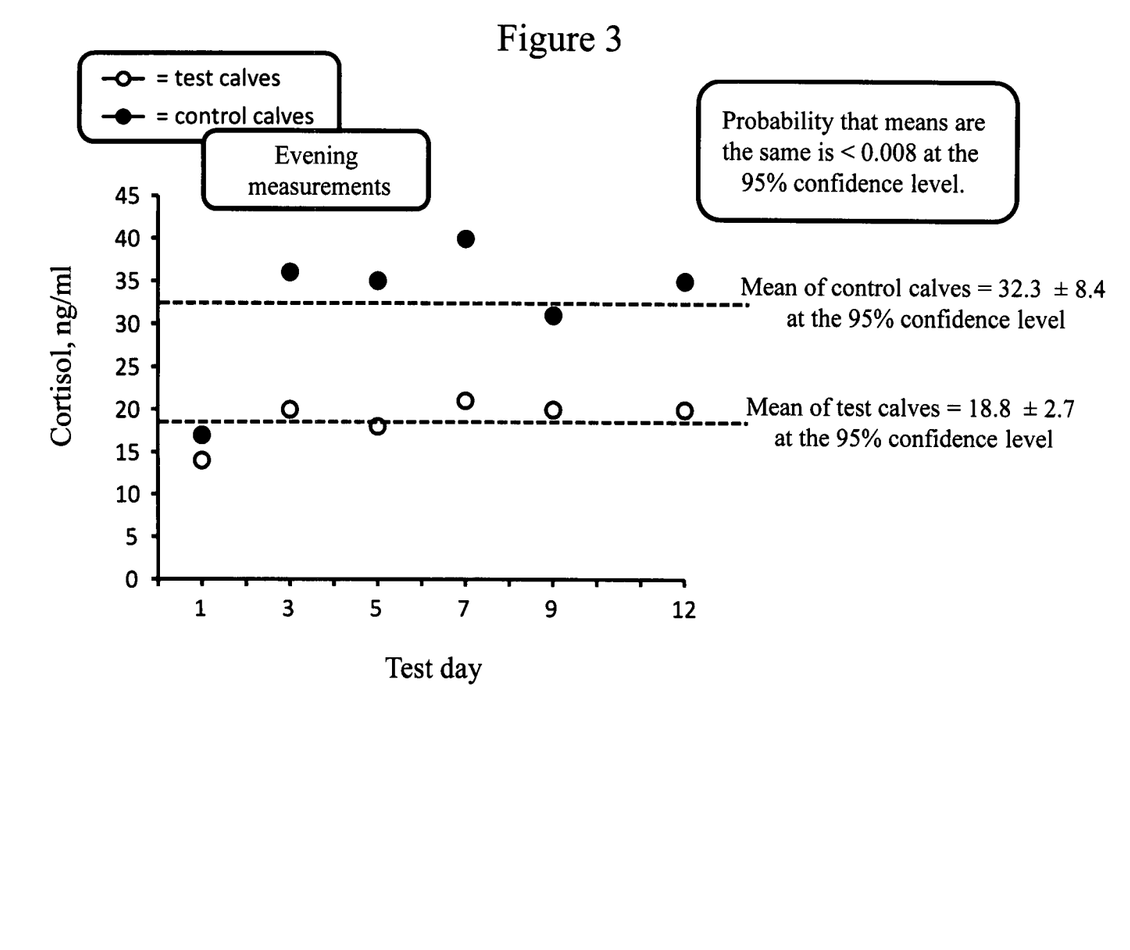
FIG. 3 graphically shows that a combination of transfer factor, lactic acid generating bacteria, and glucans reduces cortisol production in mammals. Evening cortisol is presented.
Figure 4:
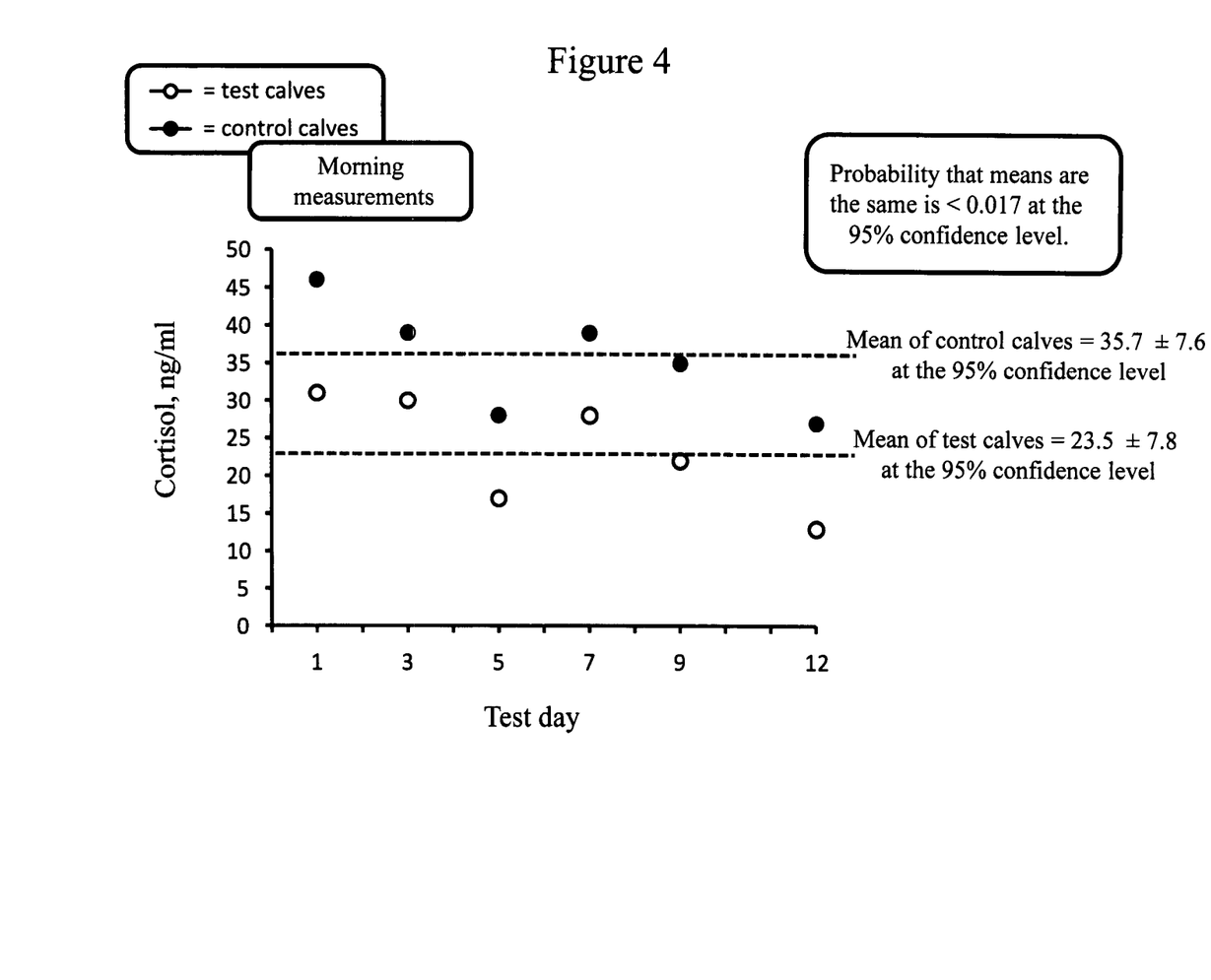
FIG. 4 graphically shows that a combination of transfer factor, lactic acid generating bacteria, and glucans reduces cortisol production in mammals. Morning cortisol is presented.

Frequency of feeding differs between animals and humans. For livestock, feeding frequency is operationally fixed. Changing the feeding frequency affects the rancher's profit. FIGS. 3 and 4 have 12 day X-axes, and reflect this economic factor.

Humans are different. Several small fertility food portions per day—rather than 1 large portion per day—is not difficult to arrange. The human guideline is effectiveness, not economics. Depending on cortisol levels throughout the day, consumption frequency may vary between five times per day and once per week.

Further, each fertility food portion throughout the day does not have to be the same. For example; a client with inherently high evening cortisol may want to purposely time consumption to decrease evening cortisol.

The method of using human fertility enhancement foods may have some or all of the following steps:
(1) determine with measurement that cortisol is higher than the population average,
(2) select the proportion of transfer factor, lactic acid generating bacteria, and glucans that comprise the mixture,
(3) choose the dosage level for the mixture,
(4) select a feeding frequency between five times per day and once per week,
(4) begin consumption before the next ovulation cycle,
(5) periodically measure cortisol levels and adjust food dosage, frequency, or both,
(6) continue consumption until a stable pregnancy is achieved, or
(7) continue consumption throughout the entire gestation period.

Some documented veterinary fertility improvements follow. They are presented to establish expectations where fertility enhancement foods are applied to human fertility utilization. There are large numbers of improved fertility cases documented for animals. Cortisol reduction is wholly or partially the reason for success. Other stress markers may also be lowered. Because the cortisol production mechanism is the same for humans and other mammals, parallel fertility successes are available to humans.

Example 1

A young bull nine months old was evaluated to have no live semen. The animal was then administered one ounce of the fertility enhancement food daily for three months. After three months, 75 ampules of viable semen were collected from the animal. This is an above average yield.

Example 2

Cattle breeding without administration of transfer factor formulation yielded about 75% conception. Addition of the transfer factor formulation increased the rate of conception to 98%. Observations were consistent with lowered cortisol.

Example 3

Thirty-five (35) mature Hampshire ewes in Santa Rosa with fertility difficulty demonstrated conception at about 40% for several years. Administration of one ounce of the transfer factor formulation on Days 6 and 7 prior to breeding increased conception to about 95%.

Example 4

A similar case was observed with donor cows. Without the fertility enhancement food, the best flush (donor) cow yielded 6 to 8 eggs; with usually only 1 or2 eggs attaining Grade 1. With the fertility enhancement food, the same cow yielded 12 eggs; 10 of these were Grade 1. Initial high cortisol was suspected due to shipping stress.

Example 5

In a commercial beef operation 100 cows were administered one ounce of fertility formulation 6 to 7 days before breeding. Conception improved by 30% with these protocols.

Example 6

Emory University has correlated both human and monkey infertility to cortisol levels. Studies are continuing.

The above animal fertility results are a very small fraction of the animal data available. A preponderance of test data supports the effect of administering transfer factor, lactic acid generating bacteria, and/or glucans to overcome infertility. Limited animal data is deemed sufficient because this instant application is focused on human fertility rather than animal fertility.

Most human studies focus on females with high cortisol. In hindsight, there is good reason for this. Miscarriages due to cortisol tend to occur in mammals within 3 weeks of conception. Any cortisol increases during the first few weeks after conception would have to be maternal because embryos cannot produce glucocorticoids during that period.

This is supported by a 2006 finding that suggests pregnancy may be particularly sensitive to maternal stress during the placentation period. The Proceedings of the National Academy of Science (Mar. 7, 2006) estimated the average time from ovulation to fetal loss in unsuccessful-pregnancies was 16 days.

It is noteworthy that most pregnancy studies document only clinical pregnancies, which are defined as 6 weeks and longer. Unfortunately, data about early miscarriage is probably under-reported.

However, the female focus does not negate the value of fertility enhancement food for males with high cortisol. The highest probability of success arises from both male and female using the fertility enhancement food.

For maximum effectiveness, formulations of (1) transfer factor and lactic acid generating bacteria or (2) transfer factor, lactic acid generating bacteria, and glucans may be utilized as a "medical food", and administered under the supervision of a health care professional. "Medical foods" is a legal term, quantified by the Federal Drug Administration in 21 CFR 101.9(j)(8).

The interaction of cortisol and fertility is shown in four figures.

Figure 1:
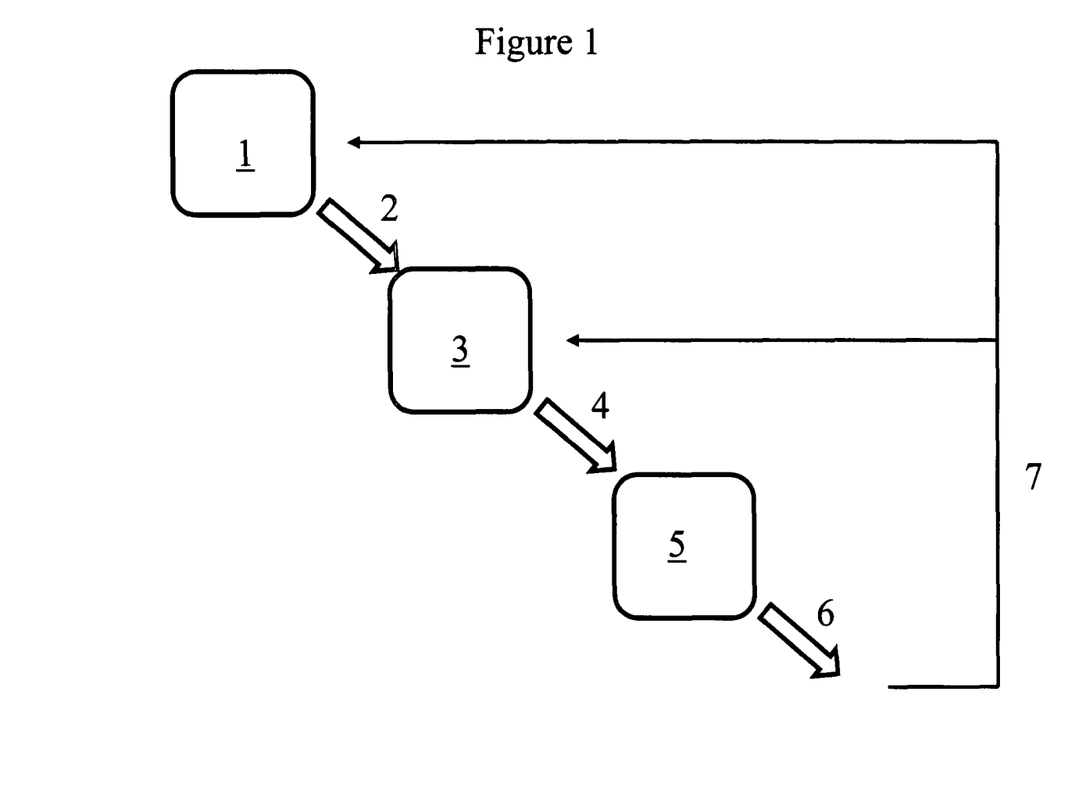
FIG. 1 is a diagram of cortisol generation in mammals.

FIG. 1 shows the cortisol production sequence. FIG. 1 applies to humans and other mammals. The hypothalamus 1 releases corticotropin releasing hormone 2, which causes the anterior pituitary gland 3 to secrete adrenocorticotropic hormone 4. Adrenocorticotropic hormone 4 travels to the adrenal cortex 5, which responds by producing cortisol 6. Levels of cortisol are controlled by negative feedback loops 7.

Figure 2:
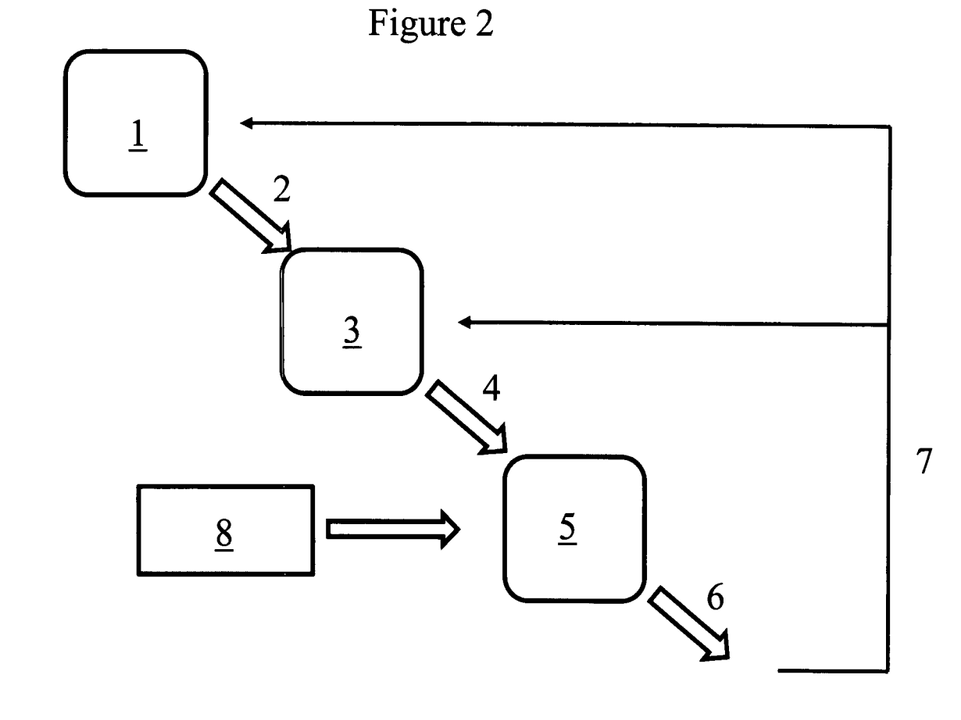
FIG. 2 is a diagram of how cortisol production consumes progesterone, which decreases the probability of a successful pregnancy.

FIG. 2 diagrams how progesterone 8 is consumed as cortisol 6 is produced by the adrenal cortex 5. The result of over-production of cortisol is sub-normal progesterone levels. This is one known cause of infertility. However, this instant application is not limited by the "progesterone steal" mechanism. Successful intervention with transfer factor, lactic acid generating bacteria, and/or glucans is based on experimental evidence rather than theory.

FIG. 3 graphically shows a drop in evening cortisol for stressed calves when fed a mixture of transfer factor, lactic acid generating bacteria, and/or glucans. This graph is provided to show how cortisol is decreased in mammals by feeding the appropriate mixture.

FIG. 4 graphically shows a drop in morning cortisol for stressed calves when fed a mixture of transfer factor, lactic acid generating bacteria, and/or glucans. As before, this graph is provided to show how cortisol is decreased in mammals by feeding the appropriate mixture.

Other stress hormones and chemical markers may also benefit from a mixture of transfer factor, lactic acid generating bacteria, and/or glucans. Examples include alpha amalyase and T4 measurements of thyroid function.

Obvious variations of the fertility method described in this application are within the scope of this application, providing that at least transfer factor and lactic acid generating bacteria are administered. Minor component range changes or use of injection does not change the principles herein.

The invention claimed is:

1. A method for improving fertility of a mammal comprising:
   providing a fertility enhancement food comprising an effective amount of transfer factor, glucans, and lactic acid generating bacteria, wherein the transfer factor comprises polypeptides with a molecular weight below 10,000 Daltons;
   determining a dosage of the fertility enhancement food based on the mammal's body weight; and
   feeding the fertility enhancement food to the mammal prior to conception.

2. The method of claim 1, wherein the mammal is a female.

3. The method of claim 2, wherein the quality or quantity of eggs of the female is increased as a result of the feeding.

4. The method of claim 1, wherein the mammal is a male.

5. The method of claim 4, wherein sperm quantity of the male is increased as a result of the feeding.

6. The method of claim 1, wherein the mammal is a human.

7. The method of claim 1 wherein the glucans are derived from natural or hybrid mushrooms.

8. A method for improving fertility of a male mammal by increasing the male's sperm count comprising: providing a fertility enhancement food comprising an effective amount of transfer factor, glucans, and lactic acid generating bacteria, wherein the transfer factor comprises polypeptides with a molecular weight below 10,000 Daltons; determining a dosage of the fertility enhancement food based on the mammal's body weight; and feeding the fertility enhancement food to the male mammal prior to conception, wherein the mammal's sperm count is increased.

9. The method of claim 8, wherein the mammal is a human.

10. The method of claim 8 wherein the glucans are derived from natural or hybrid mushrooms.

11. A method for improving fertility of a female mammal by increasing the quality or quantity of the mammal's eggs comprising:
 providing a fertility enhancement food comprising an effective amount of transfer factor, glucans, and lactic acid generating bacteria, wherein the transfer factor comprises polypeptides with a molecular weight below 10,000 Daltons;
 determining a dosage of the fertility enhancement food based on the mammal's body weight; and
 feeding the fertility enhancement food to the female mammal prior to conception, wherein the mammal's egg quality or quantity is increased relative to a control female mammal not fed the fertility enhancement food.

12. The method of claim 11, wherein the mammal is a human.

13. The method of claim 11, wherein the glucans are derived from natural or hybrid mushrooms.

14. A method for improving fertility of a mammal comprising:
 providing a fertility enhancement food comprising an effective amount of transfer factor, glucans derived from natural or hybrid mushrooms, and lactic acid generating bacteria, wherein the transfer factor comprises polypeptides with a molecular weight below 10,000 Daltons;
 determining a dosage of the fertility enhancement food based on the mammal's body weight; and
 feeding the fertility enhancement food to the mammal prior to conception.

15. The method of claim 14, wherein the mammal is a female.

16. The method of claim 15, wherein the quality or quantity of eggs of the female is increased as a result of the feeding.

17. The method of claim 14, wherein the mammal is a male.

18. The method of claim 16, wherein sperm quantity of the male is increased as a result of the feeding.

19. The method of claim 14, wherein the mammal is a human.

* * * * *